United States Patent [19]

Schwender et al.

[11] 3,936,457
[45] Feb. 3, 1976

[54] SUBSTITUTED 9-BENZYLACRIDINES

[75] Inventors: Charles F. Schwender, Lebanon; Russell E. Pike, Stanhope, both of N.J.

[73] Assignee: Warner-Lambert Company, Morris Plains, N.J.

[22] Filed: May 6, 1974

[21] Appl. No.: 467,242

[52] U.S. Cl. ............................ 260/279 R; 424/257
[51] Int. Cl.$^2$ ............ C07D 219/06; C07D 219/02; A61K 31/47
[58] Field of Search ............................... 260/279 R

[56] References Cited
OTHER PUBLICATIONS

Mizuno et al., Chemical Abstracts, Vol. 50, 1034f–1035g (1956).
Waters et al., Chemical Abstracts, Vol. 51, 9617a (1957).
Popp, Chemical Abstracts Vol. 57, 12432f(1962).
Shishido et al., Chemical Abstracts, Vol. 59, 15257c (1963).

*Primary Examiner*—Donald G. Daus
*Assistant Examiner*—Diana G. Rivers
*Attorney, Agent, or Firm*—Albert H. Graddis; Frank S. Chow; George M. Yahwak

[57] ABSTRACT

Novel, substituted 9-Benzylacridines and the methods for their preparation are disclosed. These compounds are useful in the treatment of angina pectoris.

9 Claims, No Drawings

SUBSTITUTED 9-BENZYLACRIDINES

Angina pectoris is a painful symptom of myocardial ischemia occurring when the oxygen supply cannot meet the requirements of the heart. During ischemia, pain and abnormalities of heat metabolism, left ventricular function and electrocardiograms are observed. Blood flow through the myocardium is the main determinant of oxygen supply. The heart extracts oxygen from its blood supply at near maximal efficiency so that any increase in oxygen requirements must be met by an increase in blood flow. Ischemia caused by an insufficient oxygen supply may be improved by agents which increase myocardial perfusion and reduce oxygen utilization.

Early work with nitroglycerin indicated a coronary vasodilator action which led to a concerted effort to find more potent, longer acting vasodilators selective for the coronary vascular bed. These newer agents have been disappointing since little relief of ischemia or anginal pain has been observed.

Another more recent approach to treatment of angina includes the reduction of myocardial oxygen requirements through reduced cardiac work. Also, improved circulation of blood to ischemic areas by selective dilation of certain larger supply vessels appears to restore normal oxygen and nutrient supply. Circulation through the left ventricle involves epicardial (superficial regions) and endocardial (deeper regions) pathways which compete for available blood flow from larger intramural supply vessels. Further branching of the supply vessels leads to prearteriolar, arteriolar and capillary beds which have a nutritive function in the tissues. It has been suggested that circulation in the endocardium is probably inadequate, thus establishing a relatively ischemic region. Compared with the epicardium, the endocardial region has a lower oxygen tension and a lower level of circulating nutrients. When coronary artery disease restricts blood flow, the endocardial region may be prone to myocardial insufficiency. Since the endocardium is relatively ischemic, autoregulatory responses cause an average arteriolar and precapillary sphincter dilation of about 91%. The vessels of the better perfused, epicardium are only opened about 68% and can better tolerate a decreased flow through compensatory mechanisms.

It has now been discovered that certain novel substituted 9-benzylacridines are useful in the treatment of angina pectoris due to their ability to dilate large coronary arteries which allows a preferential perfusion of the ischemic areas of the heart.

More particularly, the present invention relates to compounds of the formula:

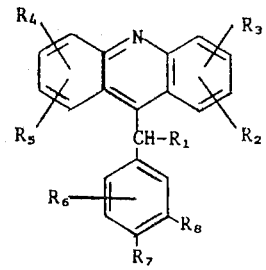

where $R_1$ may be hydrogen, nitrile, carboxamide, or carboxyalkyl; $R_2$, $R_3$, $R_4$ and $R_5$ may be separately or together hydrogen, halogen, alkyl, alkoxy, aralkyloxy, hydroxy, or methylenedioxy; $R_6$, $R_7$ and $R_8$ may be individually or collectively represented by hydrogen, halogen, alkyl, alkoxy, aralalkyloxy, methylenedioxy, or hydroxy. It may be understood that the following terms have the meaning of: halogen (Cl, Br, I, F), alkyl (1-6 carbon atoms), aralkyl (benzyl, phenylethyl, phenylpropyl where benzene ring may be optionally substituted).

In addition, suitable salts of pharmaceutically acceptable acids or bases are also included such as HCl, HBr, p-toluenesulfonate and fumarate within the bounds of the present invention.

Generally outlined, the compounds of the present invention are prepared as follows:

The appropriately substituted 9-chloroacridine is condensed with the substituted-phenylacetate in a DMF/NaH reaction mixture. While room temperature is usually sufficient for reaction, a temperature range of 0°–100° may also be employed. The $\alpha$-acridinyl-$\alpha$-phenylacetate intermediate obtained is hydrolyzed by heating in strong aqueous alkali such as 20% NaOH for about 18 hours. Acidification of the reaction mixture gives the desired substituted -9-benzylacridines as product. Reacting the 9-chloroacridines with substituted phenylacetonitrile in a DMF/NaH mixture gives the corresponding $\alpha$-acridinyl-$\alpha$-phenylacetonitrile as product. Acid hydrolysis of the nitrile gives the $\alpha$-acridinyl-$\alpha$-phenyl-carboxamide as product.

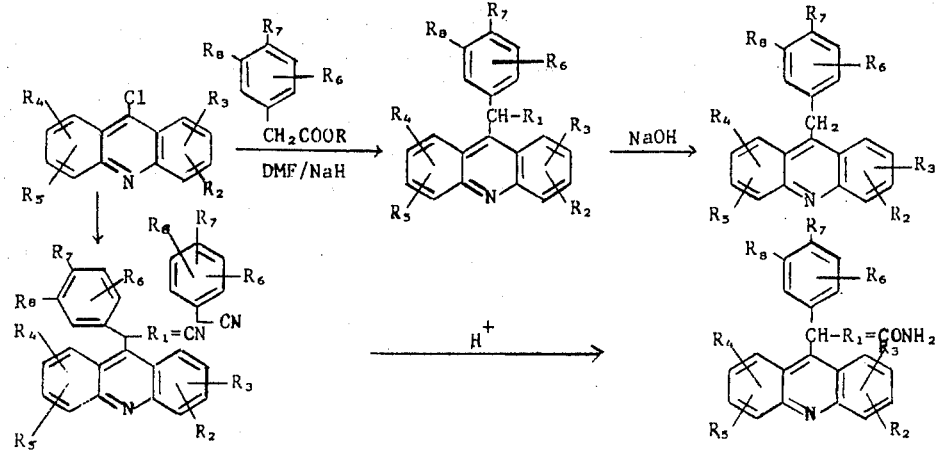

More particularly, the following examples are specific for the preparation of species under the generic invention:

EXAMPLE 1

2,3-Dimethoxy-9-veratrylacridine Hydrochloride

A reaction mixture containing 20.6 g (46.0 mmol) of methyl α-[9-(2,3-dimethoxyacridinyl)]-α-(3,4-dimethoxyphenyl)-acetate, 500 ml of MeOH and 250 ml of 20% NaOH was heated at reflux for 3 hours. The reaction mixture was cooled, acidified with HOAc and evaporated in vacuo to a residue which was partitioned between CHCl$_3$ (1 l.) and H$_2$O (500 ml). The CHCl$_3$ phase was washed with 20% NaOH (500 ml), H$_2$O (1 l.) and dried with MgSO$_4$ before evaporated in vacuo to give a crude solid residue, 15.1 g (84.4%), mp 158°–161°. The product was purified as its hydrochloride salt by recrystallization from 2-propanol; yield, 13.7 g (72.2%), mp 222°–224°.

Anal. Calcd for C$_{24}$H$_{23}$NO$_4$·HCl C, H, N, Cl.

EXAMPLE 2

9-(3,4-dimethoxy)benzylacridine

A mixture of 11.1 g (28.7 mmol) of methyl α-(9-acridinyl)-3,4-dimethoxyphenylacetate in 300 ml of MeOH and 50 ml of 20% NaOH was heated at reflux for 2 hours. The reaction mixture was cooled, acidified with HOAc and evaporated to dryness. The resultant residue was suspended in H$_2$O (250 ml) and 9.32 g (98.8%) of free base product was obtained by filtration, mp 126°–133°. The crude product was purified as the HCl salt by recrystallization from 2-propanol; yield 8.44 g (80%) mp 232°–234°.

Anal. Calcd. for C$_{22}$H$_{19}$NO$_2$·HCl C, H, N, Cl.

EXAMPLE 3

9-(3,4-diethoxybenzyl)acridine

An ethanolic solution (500 ml) containing 9.20 g (27.2 mmol) of 9-(3,4-dihydroxybenzyl)acridine hydrochloride, 4.35 g (109 mmol) of NaOH, and 50 ml of ethylbromide was stirred at room temperature for 18 hours and then refluxed for 3 hours. The reaction mixture was evaporated to a residue which was suspended between CHCl$_3$ (500 ml) and 20% NaOH (250 ml). The CHCl$_3$ phase was separated and further washed with H$_2$O (1×500 ml), dried over MgSO$_4$ and evaporated to a gummy residue. The crude product was purified as a hydrochloride salt by recrystallization from 2-propanol, mp 188°–190°.

Anal. Calcd. for C$_{24}$H$_{23}$NO$_2$·HCl·H$_2$O C, H, N, Cl.

EXAMPLE 4

9-(4-chlorobenzyl)acridine Hydrochloride

A reaction mixture containing 17.0 g (47.0 mmol) of methyl α-(9-acridinyl)-α-(4-chlorophenyl)acetate, 500 ml of MeOH and 200 ml of 20% NaOH was heated at reflux for 5 hours. The reaction mixture was cooled and acidified with HOAc before being evaporated to dryness. The resultant residue was partitioned between 750 ml of CHCl$_3$ and 250 ml of H$_2$O. The CHCl$_3$ phase was washed with 1N·NaOH (500 ml), H$_2$O (500 ml) and dried with MgSO$_4$. Evaporation of the CHCl$_3$ extract gave 13.2 g (92.2%) of the crude solid product which was purified as the HCl salt from 2-propanol; yield, 15.5 g (92.7%), mp 229°–231°.

Anal. Calcd for C$_{20}$H$_{14}$ClN·HCl·1/4C$_3$H$_8$O C, H, N, Cl.

EXAMPLE 5

Methyl α-(9-acridinyl)-3,4-dimethoxyphenylacetate

To a mixture of methyl 3,4-dimethoxyphenylacetate (19.7 g, .094 mol) 0.14 mole of NaH and 250 ml of dry DMF stirred at RT for 1 hour, was added 10.0 g (46.3 mmol) of 9-chloroacridine in 250 ml of DMF. The resultant mixture was stirred at RT for 18 hours, poured onto 1 l. ice/H$_2$O and extracted with Et$_2$O (1×500 ml) and CHCl$_3$ (1×500 ml). The combined organics were washed with H$_2$O (3×500 ml), dried over MgSO$_4$ and evaporated to give a quantitative yield of the crude product. The crude oily residue was triturated with Et$_2$O-hexane and 16.4 g (90.5%) of solid product mp 148°–154° was obtained. The analytical sample was obtained by recrystallization from MeOH/H$_2$O; yield 14.3 g, mp 157°–158°.

Anal. Calcd. for C$_{24}$H$_{21}$NO$_4$ C, H, N.

EXAMPLE 6

Methyl α-[9-(2,3-dimethoxyacridinyl)]-α-(3,4-dimethoxyphenyl) acetate

After a DMF solution (500 ml) containing 23.0 g (110 mmol) of methyl 3,4-dimethoxyphenylacetate and 164 mmol of NaH has stirred at room temperature for 1 hour, 9-chloro-2,3-dimethoxyacridine (15.0 g, 54.8 mmol) dissolved in DMF (500 ml) was added. The resultant mixture was allowed to react at room temperature for 18 hours. The resultant reaction mixture was poured onto ice/H$_2$O (2 l.) and extracted with CHCl$_3$ (1×750 ml). The CHCl$_3$ extract was washed with H$_2$O (4×1 l.) and dried over MgSO$_4$. Evaporation of the CHCl$_3$ gave a crude residue which was triturated with hexane and ether to give solid product; yield 22.5 g (91.8%), mp 114°–117° dec. The analytical sample was obtained by recrystallization from MeOH/H$_2$O, mp 118°–120° dec.

Anal. Calcd. for C$_{26}$H$_{25}$NO$_6$ C, H, N.

EXAMPLE 7

Methyl α-(9-acridinyl)-α-(p-chlorophenyl)acetate

After a mixture of DMF (250 ml), methyl p-chlorophenylacetate (25.9 g, 140 mmol) and NaH (211 mmol) was stirred at room temperature for 1 hour, 9-chloroacridine (15.0 g, 70.2 mmol) dissolved in 250 ml of DMF was added slowly. The resultant reaction mixture was stirred at room temperature for 18 hours. This reaction mixture was then poured onto 1.5 l. of an ice/H$_2$O mixture and extracted with CHCl$_3$ (500 ml). The CHCl$_3$ extract was washed with H$_2$O (3×500 ml) and dried over MgSO$_4$. Evaporation of the CHCl$_3$ extract gave a crude residual solid which was recrystallized from cyclohexane; yield, 20.2 g (79.4%), mp 192°–193°.

Anal. Calcd. for C$_{22}$H$_{16}$ClNO$_2$ C, H, N, Cl.

EXAMPLE 8

9-(3,4-dihydroxybenzyl)acridine

The 9-(3,4-benzyl)acridine 20 g (54.7 mmol) was added in small portions to previously melted pyridine hydrochloride (200 ml, at 190°–195° for 0.5 hours). The resultant mixture was heated at 190°–195° for 2 hours and then poured onto 1500 ml of ice-H$_2$O. The resultant solid was collected by filtration to give 16.2 g (87.2%) mp 265°–270° of the crude expected product. The analytical sample was obtained by recrystallization from 1-propanol, mp 283°–285°.

Anal. Calcd. for C$_{20}$H$_{15}$NO$_2$·HCl C, H, N, Cl.

Table I lists all those compounds encompassed by the generic invention. The numerical indicia preceeding specific radicals within the table refers to positions on the benzene ring at which the radical is located.

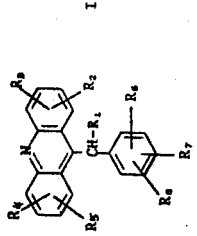

| Compound | R₁ | R₂ | R₃ | R₄ | R₅ | R₆ | R₇ | R₈ | Formula | Anal.* | mp. | Solvent Recrystn. |
|---|---|---|---|---|---|---|---|---|---|---|---|---|
| Ex. II | H | H | H | H | H | H | OCH₃ | OCH₃ | $C_{22}H_{19}NO_2 \cdot HCl$ | CHNCl | 232–234 | 2-PrOH |
| Ex. III | H | H | H | H | H | H | OC₂H₅ | OC₂H₅ | $C_{24}H_{23}NO_2 \cdot HCl \cdot H_2O$ | CHNCl | 188–190 | 2-PrOH |
| Ex. VIII | H | H | H | H | H | H | OH | OH | $C_{20}H_{15}NO_2 \cdot HCl$ | CHNCl | 283–285 | 1-PrOH |
| 09A | H | H | H | H | H | H | OCH₃ | H | $C_{21}H_{17}NO \cdot HCl$ | CHNCl | 220–222 | 2-PrOH |
| Ex. IV | H | H | H | H | H | H | Cl | H | $C_{20}H_{14}ClN \cdot HCl \cdot \frac{1}{4}C_3H_8O$ | CHNCl | 229–231 | 2-PrOH |
| 80A | H | H | H | H | H | H | CH₃ | CH₃ | $C_{22}H_{19}N \cdot HCl$ | CHNCl | 249–252 | 2-PrOH |
| 82A | H | H | H | H | H | H | Cl | Cl | $C_{20}H_{13}NCl_2 \cdot HCl$ | CHNCl | 268–270 | 1-PrOH |
| 81A | H | H | H | H | H | 2-OCH₃ | H | OCH₃ | $C_{22}H_{19}NO_2 \cdot HCl$ | CHNCl | 251–253 | 2-PrOH |
| 87A | H | H | H | H | H | H | H | OH | $C_{20}H_{15}NO \cdot HCl$ | CHNCl | 288–291 | 1-PrOH |
| 55A | H | H | H | H | H | H | OCH₃ | OCH₃ | $C_{21}H_{17}NO \cdot HCl$ | CHNCl | 230–232 | 2-PrOH |
| 54A | H | H | H | H | H | 2-OCH₃ | H | H | $C_{21}H_{17}NO \cdot HCl$ | CHNCl | 247–249 | 2-PrOH |
| 87A | H | H | H | H | H | H | O-CH₂-O | | $C_{21}H_{15}NO_2 \cdot HCl$ | CHNCl | 253–255 | 1-PrOH |
| 89A | H | H | H | H | H | OH | OH | OH | $C_{20}H_{15}NO_3 \cdot HCl$ | CHNCl | 293–294 | MeOH |
| 70A | H | H | H | H | H | H | H | H | $C_{20}H_{15}NO \cdot HCl$ | CHNCl | 299–301 | 1-PrOH |
| 37A | H | H | H | H | H | 3-OCH₃ | OCH₃ | 5-OCH₃ | $C_{23}H_{21}NO_3 \cdot HCl$ | CHNCl | 251–253 | 2-PrOH |
| Ex. I | H | 2-OCH₃ | 3-OCH₃ | H | H | H | OCH₃ | OCH₃ | $C_{24}H_{25}NO_4 \cdot HCl$ | CHNCl | 222–224 dec | 1-PrOH |
| 18A | H | 2-OCH₃ | H | 6-OCH₃ | H | OH | OCH₃ | OH | $C_{23}H_{20}ClNO_3 \cdot HCl$ | CHNCl | 264–266 dec | MeOH |
| 69A | H | 2-OH | 3-OH | H | H | H | OH | H | $C_{20}H_{15}NO_4 \cdot HCl$ | CHNCl | 323 dec | MeOH |
| 77A | H | 2-OCH | 3-OCH₃ | H | H | H | Cl | Cl | $C_{22}H_{17}Cl_2NO_2 \cdot HCl$ | CHNCl | 225–227 | 1-PrOH |
| 79 | H | 2-OCH₃ | 3-OCH₃ | H | H | H | O-CH₂-O | | $C_{23}H_{19}NO_4$ | CHN | 196–197 | 1-PrOH |
| 34 | CO₂CH₃ | 2-OCH₃ | 3-OCH₃ | H | H | H | O-CH₂-O | | $C_{25}H_{21}NO_6$ | CHN | 169–170 | MeOH–H₂O |
| 19 | CO₂C₂H₅ (6) | 2-OCH₃ | H | 6-Cl | H | H | OCH₃ | OCH₃ | $C_{25}H_{22}ClNO_5$ | CHNCl | 145–147 | C₆H₁₂ |
| Ex. VI | CO₂CH₃ | 2-OCH₃ | 3OCH₃ | H | H | H | OCH₃ | OCH₃ | $C_{26}H_{25}NO_6$ | CHN | 118–120 | MeOH–H₂O |
| 63 | CO₂CH₃ | H | H | H | H | H | Cl | Cl | $C_{22}H_{17}NO_4$ | CHN | 180–181 | C₆H₁₂ |
| 73 | CO₂CH₃ | H | H | H | H | H | CH₃ | CH₃ | $C_{22}H_{15}Cl_2NO_2$ | CHNCl | 200–202 | MeOH |
| 79 | CO₂C₂H₅ | H | H | H | H | H | CH₃ | CH₃ | $C_{25}H_{23}NO_2$ | CHN | 150–152 | MeOH–H₂O |
| 29 | CO₂CH₃ | H | H | H | H | H | 5-OCH₃ | 5-OCH₃ | $C_{22}H_{19}NO_4$ | CHN | 169–170 | 2-PrOH |
| 50 | CO₂CH₃ | H | H | H | H | 2-OCH₃ | H | H | $C_{22}H_{19}NO_3$ | CHN | 186–187 | MeOH |
| 49 | CO₂CH₃ | H | H | H | H | 2-OCH₃ | H | 3-OCH₃ | $C_{23}H_{19}NO_5$ | CHN | 195–197 | MeOH |
| 31 | CO₂CH₃ | H | 4-OCH₃ | H | H | H | OCH₃ | OCH₃ | $C_{23}H_{23}NO_5 \cdot \frac{1}{4}C_3H_8O$ | CHN | 178–180 | 2-PrOH |
| 43 | CO₂CH₃ | H | H | H | H | 3-OCH₃ | 4-OCH₃ | 5OCH₃ | $C_{25}H_{23}NO_5$ | CHN | 122–123 | C₆H₁₂ |
| 10 | CO₂C₂H₅ | H | H | H | H | H | OCH₃ | H | $C_{23}H_{19}NO_3$ | CHN | 165–166 | MeOH |
| Ex. VII | CO₂CH₃ | H | H | H | H | H | Cl | H | $C_{22}H_{16}ClNO_2$ | CHNCl | 192–193 | C₆H₁₂ |
| Ex. V | CO₂CH₃ | H | H | H | H | H | OCH₃ | OCH₃ | $C_{24}H_{21}NO_4$ | CHN | 157–158 | MeOH–H₂O |

*Satisfactory elemental analysis within ± 0.4% of theoretical was obtained for all compounds reported.

The antianginal action of this series of compounds is based upon a unique mode of action which is selective dilation of larger coronary arteries. This dilation causes a redistribution of blood flow to ischemic areas of the heart enhancing blood perfusion and reducing anoxia which causes anginal pain. (M. M. Winbury, B. B. Howe, H. R. Weiss, *J. Pharmacol. Exp. Ther.*, 176: 184 (1971)). Only nitroglycerin and some β-adrenergic blockers have demonstrated a similar redistribution of blood slow to ischemic areas by large coronary artery dilation. (M. M. Winbury, H. R. Weiss and B. B. Howe, *Eur. J. Pharmacol.*, 16: 271 (1971)).

The series of compounds of this invention offers an alternative treatment of angina without interference with adrenergic control of the heart or use of nitrates. Existing "coronary vasodilators" such as dipyridamole and chromonar dilate smaller vessels to increase coronary blood flow without redistributing flow to needed ischemic areas (H. R. Weiss and M. M. Winbury, *Fed. Proc.*, 30:(2) 631 (1971)). In severe ischemia, dipyridamole actually induced anginal attacks in man since it diverted blood flow away from ischemic areas through its dilator action on smaller coronary vessels. (O. Mantero and F. Conti, *Circulatory Drugs*, A. Bertelli, ed. pp 118–123, North-Holland, Amsterdam, The Netherlands, 1969; C. F. Schwender, "Antianginal Agents", Ann. Rep. Med. Chem., 7: 69, R. V. Heinzelmann, ed. Academic Press, New York, 1972).

Experimentally, this flow redistribution can be demonstrated in a dog by measuring changes in resistance to blood flow of larger coronory arteries (RL) to ischemic tissue relative to smaller vessel resistance to flow (RT) in normal tissue. Analogs of this invention caused a decrease in the ratio RL/RT similar to that observed with nitroglycerin.

Generally, a dose of 1–5 mg/kg, iv was required to demonstrate a drop in RL/RT in dogs. Coronary vasodilators such as dipyridamole and chromonar caused an increased RL/RT ratio reflecting the redistribution of blood flow away from ischemic areas.

We claim:
1. A substituted 9-benzylacridine of the general formula:

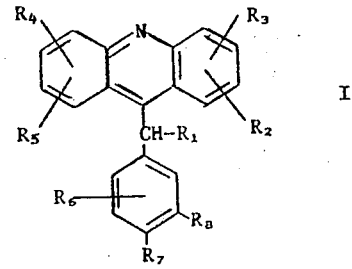

$R_1$ is selected from the group consisting of
- —H,
- —$CO_2CH_3$;

$R_2$ is at the number 2 carbon on the acridine ring and is selected from the group consisting of
- —$OCH_3$,
- —H;

$R_3$ is selected from the group consisting of
- —$OCH_3$,
- —H;

$R_4$ is
- —H;

$R_5$ is
- —H;

$R_6$ is
- —H;

$R_7$ is selected from the group consisting of
- —$OCH_3$,
- —OH,
- —$OC_2H_5$,
- —Cl;

$R_8$ is selected from the group consisting of
- —$OCH_3$,
- —OH,
- —$OC_2H_5$,
- —H.

2. The compound of claim 1 which is 2,3-dimethoxy-9-veratrylacridine hydrochloride.

3. The compound of claim 1 which is 9-(3,4-dimethoxy)benzylacridine.

4. The compound of claim 1 which is 9-(3,4-diethoxybenzyl)acridine.

5. The compound of claim 1 which is 9-(4-chlorobenzyl)acridine hydrochloride.

6. The compound of claim 1 which is methyl α-(9-acridinyl)-3,4-dimethoxyphenylacetate.

7. The compound of claim 1 which is methyl α-[9-(2,3-dimethoxyacridinyl)]-α-(3,4-dimethoxyphenyl)acetate.

8. The compound of claim 1 which is methyl α-(9-acridinyl)-α-(p-chlorophenyl)acetate.

9. The compound of claim 1 which is 9-(3,4-dihydroxybenzyl)acridine.